United States Patent
Höjer

(10) Patent No.: US 11,534,082 B2
(45) Date of Patent: Dec. 27, 2022

(54) SYSTEM FOR COLLECTING EXHALED PARTICLES

(71) Applicant: PEXA AB, Gothenburg (SE)

(72) Inventor: Svante Höjer, Kungälv (SE)

(73) Assignee: PEXA AB, Gothenburg (SE)

( * ) Notice: Subject to any disclaimer, the term of this patent is extended or adjusted under 35 U.S.C. 154(b) by 146 days.

(21) Appl. No.: 16/628,844

(22) PCT Filed: Jul. 4, 2018

(86) PCT No.: PCT/EP2018/068117
§ 371 (c)(1),
(2) Date: Jan. 6, 2020

(87) PCT Pub. No.: WO2019/011750
PCT Pub. Date: Jan. 17, 2019

(65) Prior Publication Data
US 2020/0221973 A1   Jul. 16, 2020

(30) Foreign Application Priority Data

Jul. 10, 2017 (SE) .................................... 1750908-4

(51) Int. Cl.
*A61B 5/08* (2006.01)
*A61B 5/097* (2006.01)
*G01N 33/497* (2006.01)

(52) U.S. Cl.
CPC .............. *A61B 5/097* (2013.01); *A61B 5/082* (2013.01); *G01N 33/497* (2013.01); *A61B 2560/02* (2013.01); *A61B 2560/04* (2013.01); *G01N 2033/4975* (2013.01)

(58) Field of Classification Search
CPC ..... A61B 5/097; A61B 5/082; A61B 2560/02; A61B 2560/04; G01N 33/497; G01N 2033/4975
See application file for complete search history.

(56) References Cited

U.S. PATENT DOCUMENTS

| | | | |
|---|---|---|---|
| 2010/0276100 A1 | 11/2010 | Tamai et al. | |
| 2010/0297635 A1* | 11/2010 | Olin | A61B 5/411 435/6.11 |
| 2013/0345586 A1* | 12/2013 | Fisher | A61B 5/14551 600/532 |

(Continued)

FOREIGN PATENT DOCUMENTS

| | | |
|---|---|---|
| EP | 0833156 A1 | 4/1998 |
| WO | WO2009045163 A1 | 4/2009 |

(Continued)

OTHER PUBLICATIONS

Search Report from Swedish Patent App. No. 1750908-4 (dated Mar. 15, 2018).

(Continued)

*Primary Examiner* — Andrey Shostak
(74) *Attorney, Agent, or Firm* — Cermak Nakajima & McGowan LLP; Malcolm K. McGowan

(57) ABSTRACT

The disclosure pertains to a system 100 and method for collecting and measuring particles in exhaled air. The system 100 is arranged to allow for examination of the full or substantially the full volume of each exhalation of a subject.

14 Claims, 9 Drawing Sheets

(56) References Cited

U.S. PATENT DOCUMENTS

| | | | | |
|---|---|---|---|---|
| 2014/0228699 A1* | 8/2014 | Causevic | ............... | A61B 5/087 |
| | | | | 600/532 |
| 2014/0288454 A1* | 9/2014 | Paz | ...................... | A61B 5/4845 |
| | | | | 600/532 |
| 2014/0358019 A1* | 12/2014 | Johnson | ................. | A61B 5/082 |
| | | | | 600/532 |
| 2015/0033824 A1 | 2/2015 | Hammarlund et al. | | |

FOREIGN PATENT DOCUMENTS

| WO | WO2012/006250 A1 | 1/2012 |
|---|---|---|
| WO | WO2013/095284 A1 | 6/2013 |
| WO | WO2013/117747 A1 | 8/2013 |
| WO | WO2014/165184 A1 | 10/2014 |
| WO | WO2017/001217 A1 | 1/2017 |

OTHER PUBLICATIONS

International Search Report for PCT Patent App. No. PCT/EP2018/068117 (dated Oct. 23, 2018).

International Preliminary Report on Patentability for PCT Patent App. No. PCT/EP2018/068117 (dated Jul. 2, 2019) with Annex and Amended Claims.

\* cited by examiner

SYSTEM FOR COLLECTING EXHALED PARTICLES

CROSS-REFERENCE TO RELATED APPLICATIONS

The present application is a National Stage Entry under 35 USC 371 of PCT/EP2018/068117, filed Jul. 4, 2018, which claims priority from Swedish patent applications 175908-4, filed Jul. 10, 2017. The contents of these priority applications are incorporated herein by reference in their entirety.

TECHNICAL FIELD

The present disclosure pertains to a system for collection and measurement of particles in exhaled breath of a subject such as a human or an animal. The present disclosure also pertains to the use of such a system for determination of a medical condition of a subject.

BACKGROUND

The human airways are daily confronted with at least 7-8 cubic meters of air and there is an advanced biological system to detoxify inhaled particles and gases. The first line defence against inhaled material is the Respiratory Tract Lining Fluid (RTLF), covering all the airways, among other things containing several important antioxidant systems. Another important component of the RTLF is a surfactant, containing compounds for decreasing surface tension but also taking part in the innate immunity.

The composition of RTLF has been shown to change in inflammatory conditions of the airways. When the balance between anti-oxidants in RTLF and inhaled oxidants is disturbed, oxidative stress will initiate an inflammatory process. This inflammatory process, although very variable, is a major early event which is common in the development of most respiratory diseases, from asthma to lung cancer.

The patho-physiological processes leading to respiratory diseases are so far not fully understood. One reason for this is that those processes are difficult to monitor in humans. Examples of methods used to evaluate the effect of various exposures include measurement of lung-function, exhaled nitric oxide, induced sputum or analysis of broncho-alveolar lavage (BAL) or biopsies from bronchoscopy. Unfortunately, these methods are associated with disadvantages such as being too invasive, provision of variable results and/or involving risks.

Further methods used include in-vitro studies, which only allow limited generalizations to the complex environment of human airways. The same is to a large extent true for animal studies, where—although genetic concordance to humans is high—the expression of various genes differs substantially.

Still a further method that has been introduced is collection of exhaled breath condensate (EBC) i.e. exhaled water vapour that is condensed by the means of low temperature, where both volatile and non-volatile compounds have been identified. The non-volatiles found in EBC are believed to originate from particles formed within the airways. The collection of exhaled breath condensate (EBC) is connected with a number of serious methodological difficulties such as dilution with water resulting in very low concentrations of the substances of interest, high contamination with substances originating from the oral cavity, high intra-individual coefficient of variation and a very inefficient way to sample the non-volatiles found in EBC.

Various systems for analysis of a subject's breath have been proposed some of which include a reservoir for temporary storage of exhaled breath and/or provide for stepwise collection of the exhaled breath followed by analysis of said exhaled breath.

US20100276100 discloses a system provided for sensing an analyte in a breath sample. The system includes a breath bag, a cartridge and a base. The breath bag contains the breath sample. The bag includes a mouthpiece fixedly disposed on the breath bag. The cartridge includes an interactant that reacts with the analyte and generates a change in an optical characteristic relative to a reference.

US20130345586 discloses a method and a device for measuring cardiac related parameters non-invasively via the lung during spontaneous and controlled ventilation of a subject. The device includes a breathing unit comprising an expiratory reservoir bag. Excess of exhaled breath from a subject exits the expiratory reservoir bag via an opening to ambient air.

EP 0 833 156 discloses a method for detecting a variation, such as a variation in the concentration of a substance, in a flowing medium, whereby a sample of the medium is made to flow past a sensor (for detecting the variation, the direction of flow of the sample is reversed and the velocity of the sample in relation to the sensor is reduced during the samples passage through the sensor. Thus, a device for detecting such a structure or variation contains a sensor and means for reversing the direction of flow and reducing the velocity of the sample of the medium.

US20140228699 discloses methods and systems to obtain and analyse one or more gas samples from the breath of a person, and organizing the samples in a sample registry for subsequent analysis.

WO 2013/095284 discloses a device for measuring a component in exhaled breath comprising an inlet for receiving exhaled breath, a buffer chamber and a sensor. Part of the exhaled air by-passes the sensor.

WO 2009/045163 discloses a method and a system for collection and measurement of exhaled particles. The system includes a reservoir which supplies air to an impactor when no exhalation is taking place. Moist particle-free air is added to the reservoir so that there is always a positive discharge flow.

Since subjects suffering from impaired lung function frequently experience difficulties in breathing it would be desirable to alleviate their efforts during physical examination such as diagnosis while maintaining or improving examination quality. For instance, a shorter time and/or a reduced number of exhalations involved in physical examination would be advantageous. Additionally or alternatively, from a health care system perspective improving the efficiency with respect to quality and/or time for examination and/or treatment is always desired.

Hence, there is a need for alternative and/or improved systems and/or methods.

SUMMARY

It is an object of the present disclosure to provide a system and/or method that overcomes or at least mitigates disadvantages associated with known systems and/or methods in the art. Further, it is an object of the present disclosure to provide an alternative to current systems and/or methods in the art.

According to the present disclosure, there is provided a system for collecting exhaled particles, in accordance with claim 1. Further embodiments are set out in the dependent claims, in the following description and in the drawings.

The present disclosure provides:
a system for collecting exhaled particles, said system comprising:
a) a reservoir having first opening and a second opening;
b) a mouthpiece,
c) an inertial impactor having an inlet and an outlet, said impactor being arranged to pass a gas stream A comprising particles P between said inlet and said outlet, said inlet of said inertial impactor being connected to the first opening of the reservoir,
d) a pump having an inlet and an outlet, the pump being arranged to maintain a constant gas stream flow through the impactor, and
e) a first valve.
wherein
said first opening of said reservoir is connected to said mouthpiece via said first valve,
said pump is located downstream of said impactor,
said second opening of said reservoir is connected to said outlet of said pump.

The system is arranged to maintain a constant flow of air exhaled through the impactor by means of a pump. The air exhaled by the subject passes through the mouthpiece and enters the inertial impactor, and also the reservoir since the impactor capacity usually is insufficient for handling an entire exhalation at a time. Thus, the exhaled air exceeding the impactor capacity enters the reservoir. When the subject finishes his/her exhalation the first valve is closed. The pump will then draw the exhaled air stored in the reservoir through the impactor. In this way, a continuous flow of exhaled air through the impactor is maintained and a large part of the exhaled air stored in the reservoir such as substantially all of the stored exhaled air will be drawn through the impactor. When a subject then exhales into the system through the mouthpiece the process starts all over again. Thus, it can be seen that a large part such as most or substantially all of the exhaled air is used in the system. The full or substantially the full volume of each exhalation of a subject is examined. The system may be operated without requiring external air to be added to the reservoir to maintain a flow through the system thereby reducing a risk for contamination associated with added external air, i.e. the system may be configured to be operated without adding external air The system of the present disclosure may further comprise a second valve. The second opening of the reservoir may then be connected to the outlet of the pump upstream of the second valve. The second valve is closed unless air is exhaled into the system.

The presence of a second valve may function as a safety measure to ensure that no external air enters the system. However, it has been found that the presence of only the first valve is sufficient. Additionally, a system as disclosed herein including only a first valve has been perceived by some users such as users with impaired or severely impaired lung capacity to provide less resistance to exhalation compared to a system as disclosed herein including a first valve and a second valve.

It is a significant benefit that the system described herein allows for performing analysis of a subject's breath in a continuous way, i.e. the impactor is fed with exhaled air continuously from the mouthpiece and/or the reservoir.

In order to maximize the use of the exhalations, the reservoir volume may be selected to match the lung volume of the subject undergoing examination. The average total lung capacity of an adult human male is about 6 litres of air. The residual lung volume, i.e. the lung volume after exhalation, is about 1 litre of air. Thus, if the impactor capacity, i.e. the volume of air that the impactor can take in, is about 1 litre then a suitable reservoir volume may be about 4 litres. However, the lung capacity between subjects may vary. It will be appreciated that the choice of reservoir volume may depend on impactor flow rate capacity and/or the volume of air exhaled by a particular subject undergoing examination. Examples of suitable reservoir volumes include 2-7 litres such as 2 litres, 3 litres, 4 litres, litres, 6 litres and/or 7 litres. Conveniently, the reservoir may be removably attached to the system disclosed herein to allow for selecting and connecting a reservoir with a suitable volume. Thus, the reservoir may be replaceable. In this document, the reservoir volume refers to the internal volume of the reservoir.

The reservoir may be made of any inert material such a material suitable for medical applications. The material may be stiff.

The mouthpiece may be arranged to allow for all or substantially all of the breath exhaled by a subject to pass through the mouthpiece and enter the inertial impactor and/or reservoir. Further, the mouthpiece may be a two-way mouthpiece allowing a subject to inhale and/or exhale air through the two-way mouthpiece. Upon inhalation the inhaled air may pass a filter such as a particle filter. The use of a filter minimizes contamination of the inhaled air with components such as particles. Of course, such a contamination may have a negative impact on the examination of a subject's lungs.

The system described herein may include further particle filters. For instance, a particle filter may be present downstream of the pump. Additionally or alternatively, a particle filter may be associated with the two-way mouthpiece in such a way that it allows a subject to inhale air having passed said filter.

The system disclosed herein may further comprise one or more flow meters such as a first flow meter, a second flow meter and/or a third flow meter.

The first flow meter may be arranged to measure the flow through the inertial impactor and the pump and/or control the flow of the gas stream passing through the impactor. The first flow meter may be arranged downstream of the pump.

The second flow meter may be arranged to measure the total volume of an exhalation by a subject. Further, the second flow meter may be arranged upstream of the second valve. The third flow meter may be arranged to measure the air flow inhaled by a subject.

The first valve and, when present, the second valve may independently be a manually operated valve or a one-way valve. Conveniently, however, the first valve and, when present, second valve are one-way valves. It will be appreciated that a one-way valve is a valve that allows a fluid such as liquid or gas to flow through it in only one direction. In a further example, the second valve may be omitted.

The system disclosed herein may include a further valve located downstream of the first valve and upstream of the impactor and the reservoir. The further valve may be arranged to be operated manually. Alternatively, the further valve may be a one-way valve.

The system disclosed herein may further include a line for gas such as air or air mixed with a pharmaceutical. The line for gas, i.e. gas line, may include a particle filter, a flow meter and/or a one-way valve arranged to allow for gas to enter into the system. For instance, the gas line may include a one-way valve and optionally a particle filter. The gas line may be coupled to the system between the mouthpiece and the first valve. In a further example, the line for gas may be located downstream of the mouthpiece and upstream of the first valve. Further, the gas line described herein and the mouthpiece described herein may be provided as a three-way coupling element.

An advantage of the system of the present disclosure is that the exhaled air and particles are substantially unaffected between leaving the subject and entering the impactor. As a consequence, analysis may take place on non-modified or substantially non-modified particles allowing for a more accurate determination and/or diagnosis.

In order to minimize the risk of modifying the particles in the exhaled air the components of the system may be thermostatted. For example, the mouthpiece, impactor and/or reservoir may be thermostatted. In an example, at least part of the system may be arranged in a thermostatted compartment. For instance, the mouthpiece, the inertial impactor and/or the reservoir may be located in the thermostatted compartment. This has the advantage that the size distribution of the particles of the exhaled air, which may be an aerosol, is affected to no or only a limited extent by evaporation and/or condensation of water vapour. As a result, the components such as particles originating from the subject's lungs are measured in a state identical or nearly identical to that in the lungs. Thereby, a very accurate account of the state of the lungs is provided.

To further increase the accuracy of measurements made using the system of the present disclosure the mouthpiece may be kept at a temperature such that the size distribution of the components such as particles of the exhaled air is affected to no or only limited extent by evaporation and/or condensation of water vapour. This may be achieved by thermostatting the mouthpiece. For instance, the major part of the mouthpiece may be placed in a thermostatted compartment while still allowing a subject to inhale and/or exhale through the mouthpiece The mouthpiece or at least part of the mouthpiece may be located in a thermostatted compartment together with the impactor and the reservoir.

The system described herein may further comprise a particle counter allowing for supplying additional information such as particle counting and/or number size distributions. The particle counter may be a Grimm 1.108 optical particle counter (Grimm Aerosol Technik, Ainring, Germany), capable of counting, and sizing particles in 15 size intervals from 0.3 to 20 micrometer. The particle counter may provide a number size distribution of the measured aerosol or a mass distribution, calculated from the measured number size distribution. In the instrument, air containing particles may be passed through a small, well defined, intensely illuminated volume in a manner so that only one particle at a time is illuminated. The illuminated particle give rise to a pulse of scattered light, the intensity of which is measured. Since the intensity of scattered light depends on the particle size, it is possible to count and size the particles in the air stream. The particle counter may be connected with the impactor. For example, the particle counter may be located just before the impactor. The particle counter may also be arranged to allow for returning the air passing through said particle counter to the system.

The inertial impactor may be any inertial impactor known in the art suitable for use in a medical application. The inertial impactor, which may also be denominated cascade impactor, functions based on the principle of inertial impaction i.e. separation is provided on the basis of differences in inertia—a function of particle size and velocity. As an example, the system of the present disclosure may comprise an inertial impactor comprising:

an inlet and an outlet, the impactor comprising a plurality of stages arranged such that a gas stream comprising particles enters the impactor via the inlet and passes through each stage in turn before exiting the impactor via the outlet; wherein each stage is separated from adjacent stages by a partition having an orifice which directs the primary gas stream towards collection plates, the major face of each collection plate being arranged substantially perpendicular to the direction of flow of the gas stream; the inlet of the inertial impactor being connected to the first opening of the reservoir.

The collection plates may have a thickness of from about 0.4 micrometer to about 1 micrometer. The collection plates may be square shaped with 10-12 mm side. In a further example, the collection plates may have a circular shape optionally with a diameter of about 25 mm. The plates may be held in place on the substrate holders by double sided tape at the exit of the air streams through the nozzles. The plates may be made of elemental silicon since this is favourable for the ensuing analysis. Additionally or alternatively, the collection plates may have a modified surface adapted for the intended analysis. The plates must be clean since trace amounts of impurities may interfere with the ensuing analysis of the particles. The cleaning of the silicon plates may be done in several ways such as by ultrasonic cleaning in organic solvents followed by UV-ozone treatment, or by immersion in 1-10% nitric acid or hydrogen peroxide. Examples of collection plate surfaces include hydrophilic polytetrafluoroethylene, hydrophilic glass fiber, hydrophilic mixed cellulose esters, hydrophobic polyvinylidene fluoride, hydrophilic polycarbonate and hydrophilic silicon wafer. The collection plate(s) may be a membrane including the collection plate surfaces described herein.

The impactor collection plates may be removed and analysed as to their chemical content. The analysis may be performed while the exhaled air components and/or particles remain on the plates and/or after the exhaled air components and/or particles have been removed from the plates. The analysis may be performed using standard analytical techniques as known in the art. The analysis will then provide an insight into the medical condition of the subject undergoing examination. The kind of particles and/or the particle distribution profile with respect to, for instance, mass will provide valuable information that can be used in the analysis. For instance, some of the particles may be biomarkers for certain medical conditions. By comparing with data obtained from a subject having or not having a medical condition a conclusion may be made about the medical indication of the subject undergoing examination. Additionally or alternatively, an analysis using the system disclosed herein may be used under different circumstances for the same subject in order to monitor a medical condition.

It will be appreciated that the flow meter 119, the filter 121 and/or the flow meter 122 described herein may be optional. Thus, the present disclosure provides a system 100 as described herein lacking the flow meter 119, the filter 121 and/or the flow meter 122.

There is also provided a use of the system of the present disclosure for determining a medical condition of a subject. The system may then be used for identifying, for instance, a biomarker that is associated with a medical condition. The medical condition may be a disease and/or a medical disorder. The biomarkers may be at least one of proteins, phospholipids, bacteria, viruses, RNA, DNA. Examples of biomarker proteins include Sp-A, Sp-B, Sp-C, Sp-D, TNF-alpha, CC10 (CC16), Albumin, Fibronectin, Fibrinogen, SAP, A2M, CRP, Haptoglobin, AGP, Alpha-1-antitrypsin, KI-6 and Transferrin. In this document, Sp means surfactant protein and KL-6 means Krebs von den Lungen 6 glycoprotein. Examples of phospholipids include DPPC (dipalmitoylphosphatidylcholine), phosphatidylglycerol (PG28:1, PG28:0, PG32:0, PG34:1, PG36:2, PG36:1), phospatidylcholine (PC28:0, PC30:0, PC32:0, PC32:1, PC34:1), phosphatidylinositol (PI34:2, PI34:1, PI36:2, PI36:1), and phosphatidic acid (PA32:1, PA32:0). The biomarker RNA or DNA may be entire RNA or DNA or fragments thereof.

Examples of medical conditions that may be determined and/or monitored using the system of the present invention may be selected from one or more of the group consisting of asthma bronchiale, cystic fibrosis, chronic obstructive pulmonary disease (COPD), interstitial lung-disease, sarcoidosis, pulmonary engagement in systemic disease, pulmonary infections such as pneumonia, bacterial colonization, viral infections, heart failure, hypercholesterolemia, diabetes, metabolic syndrome, condition associated with organ transplant rejection, and increased genetic susceptibility to disease or exposure.

BRIEF DESCRIPTION OF THE DRAWINGS

The present disclosure is further illustrated with reference to the appended drawings in which.

It is to be understood that the drawings are schematic and that individual components are not necessarily drawn to scale.

DETAILED DESCRIPTION OF EMBODIMENTS

Figure 1:
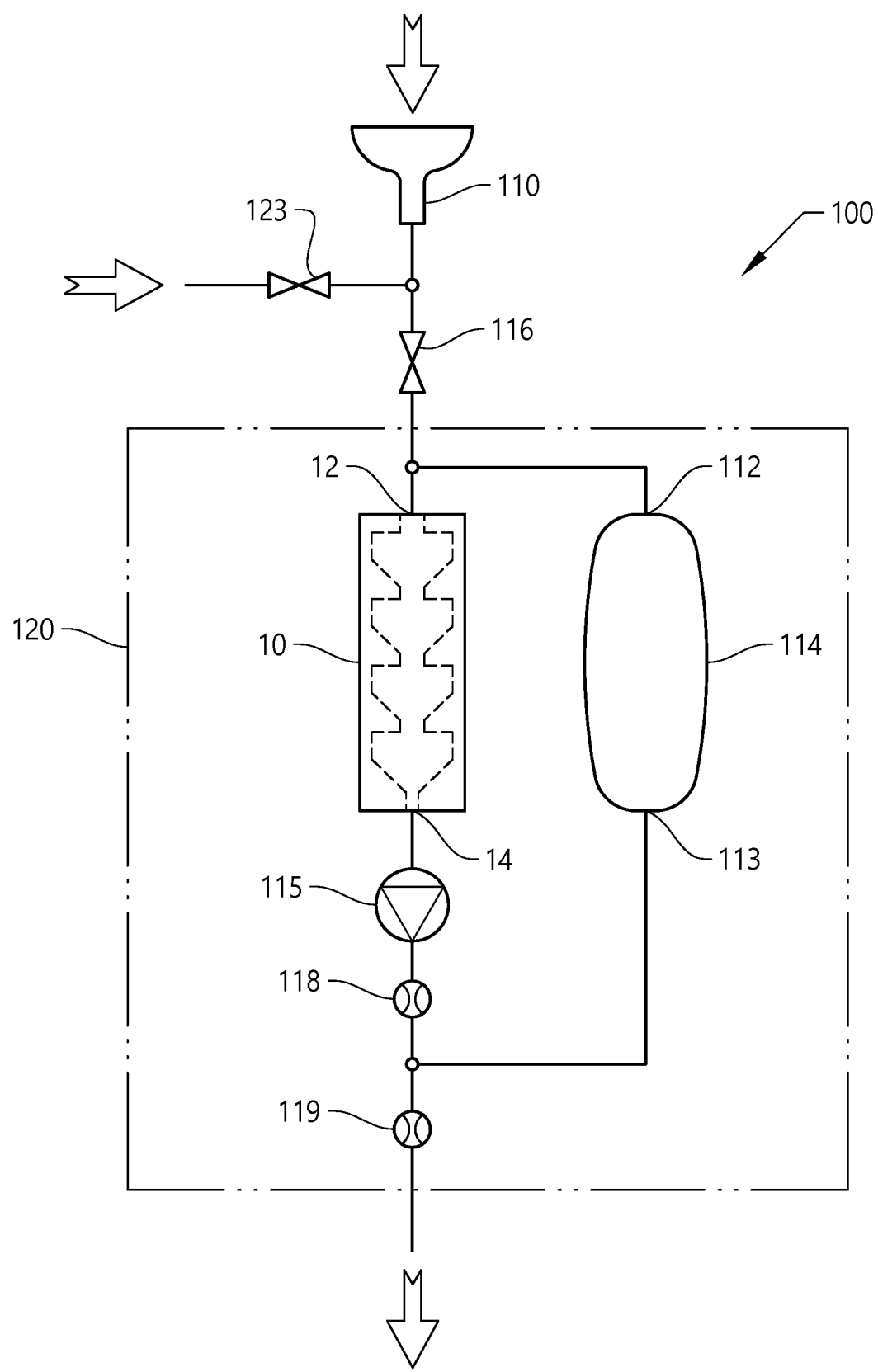
FIG. 1 shows a system 100 for collection of exhaled particles.

FIG. 1 shows a system 100 comprising a mouthpiece 110, an inertial impactor 10, a reservoir 114 and a pump 115. The system further comprises a first valve 116, a first flow meter 118 and a second flow meter 119. The inlet 12 of the inertial impactor 10 is connected to the first opening 112 of the reservoir 114. The first opening 112 of the reservoir is also connected with the mouthpiece 110 via the first valve 116. The mouthpiece 110 may be a two-way mouthpiece. The first valve 116 may be a one-way valve. The second opening 113 of the reservoir 114 is connected to the outlet of the pump 115 and is downstream of the first flow meter 118 and upstream of the second flow meter 119. Part of the system is located within a thermostatted compartment 120. The system further comprises a line for gas including a one-way valve 123.

Figure 2:
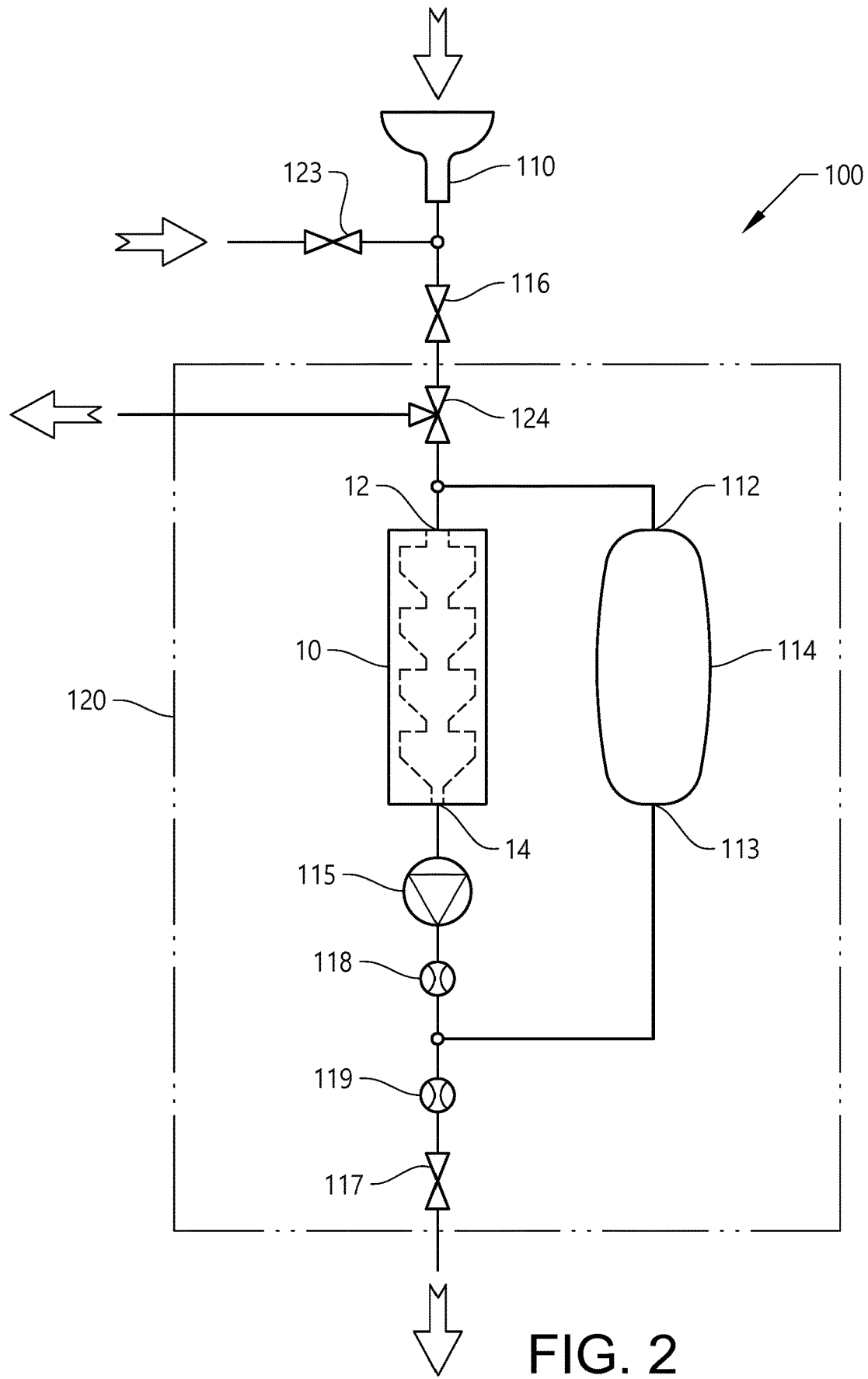
FIG. 2 shows the system 100 of FIG. 1 further comprising a second valve 117, and a valve 124.

FIG. 2 shows the system 100 of FIG. 1 further comprising a second valve 117, and a valve 124. The second valve 117 is located downstream of the second flowmeter 119, and may be a one-way valve or a manually operated valve. The valve 124 is located within the thermostatted compartment 120 and may be a manually operated valve or a one-way valve. The valve 124 may be configured to allow air to enter the impactor 10 and/or the reservoir 114, or to be let out of the system.

Figure 3:
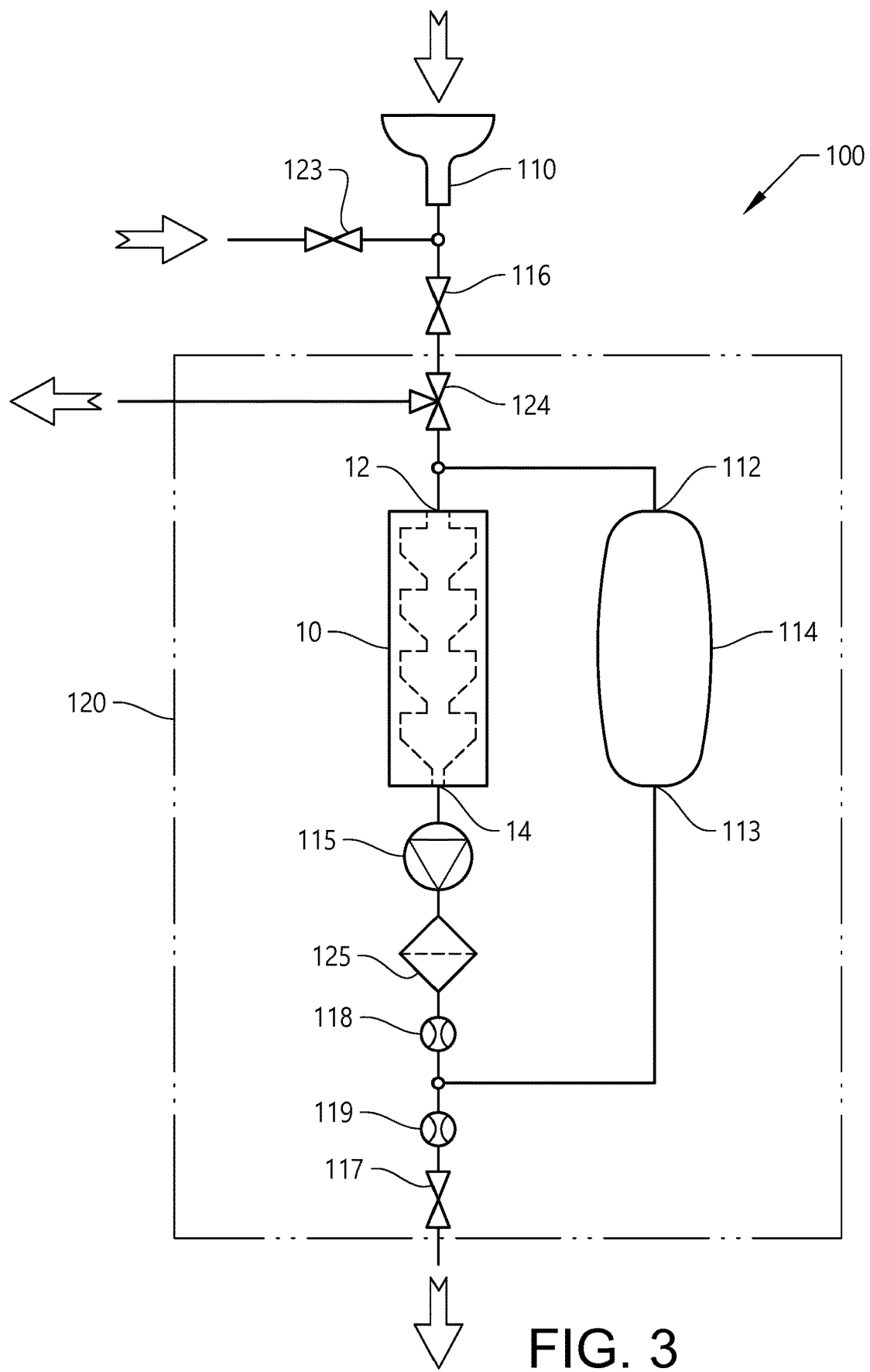
FIG. 3 shows the system 100 of FIG. 2 further comprising a particle filter 125.

FIG. 3 shows the system 100 of FIG. 2 further comprising a particle filter 125 located between the pump 115 and the first flow meter 118.

Figure 4:
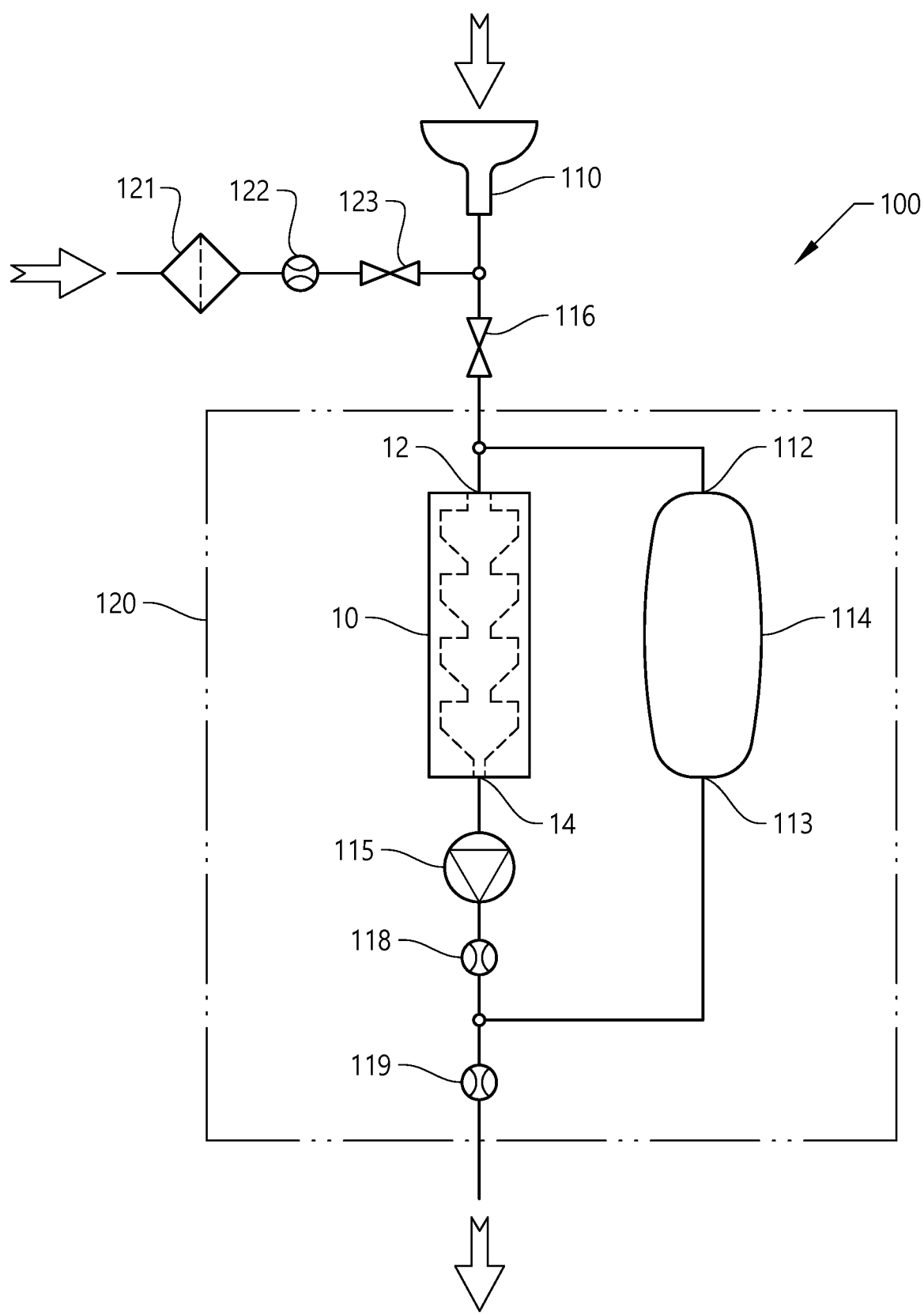
FIG. 4 shows the system 100 of FIG. 1 further comprising a particle filter 121 and a flow meter 122.

FIG. 4 shows the system 100 of FIG. 1 further comprising a particle filter 121 and a flow meter 122.

Figure 5:
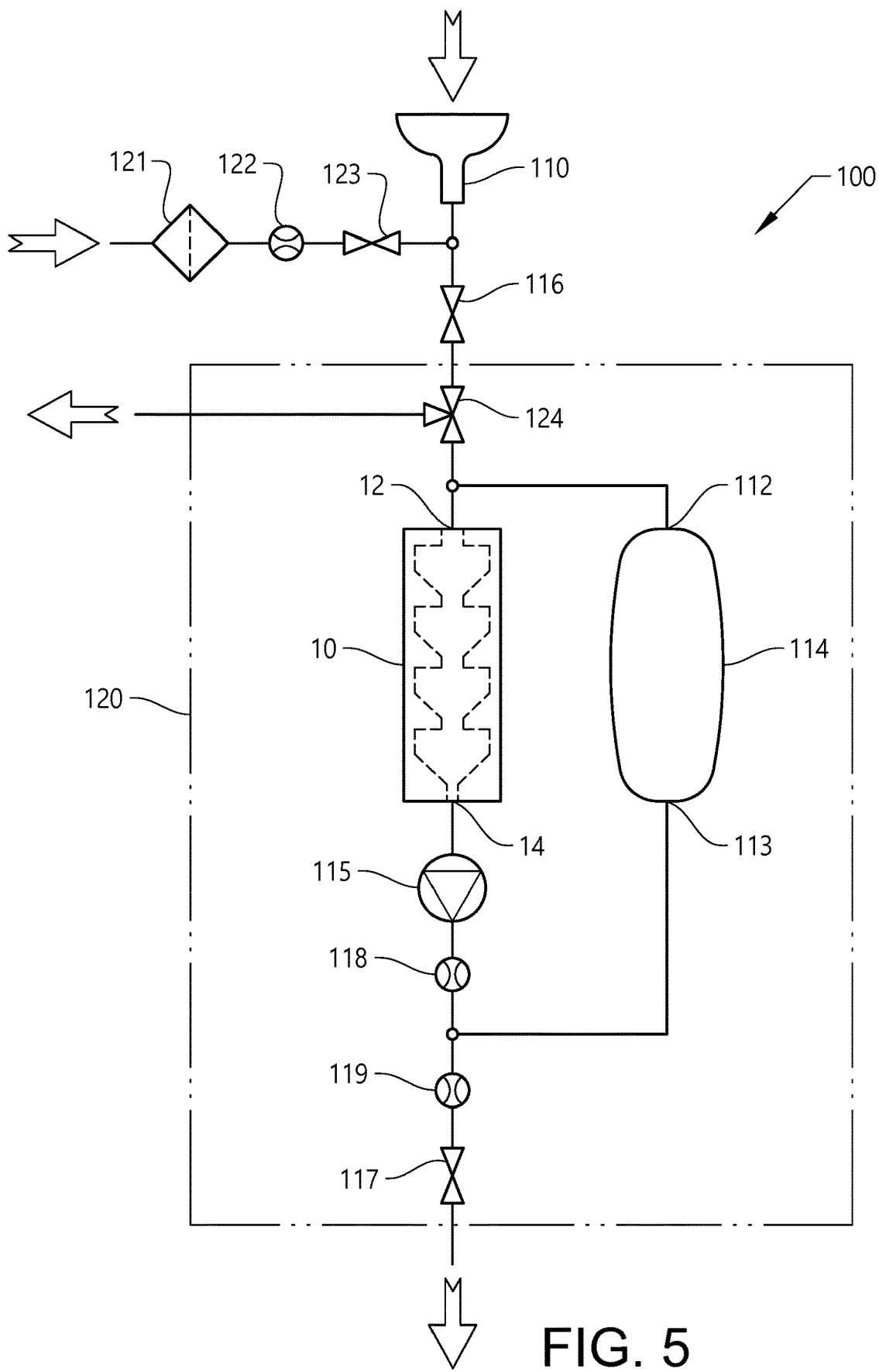
FIG. 5 shows the system 100 of FIG. 2 further comprising a particle filter 121 and a flow meter 122.

FIG. 5 shows the system 100 of FIG. 2 further comprising a particle filter 121 and a flow meter 122.

Figure 6:
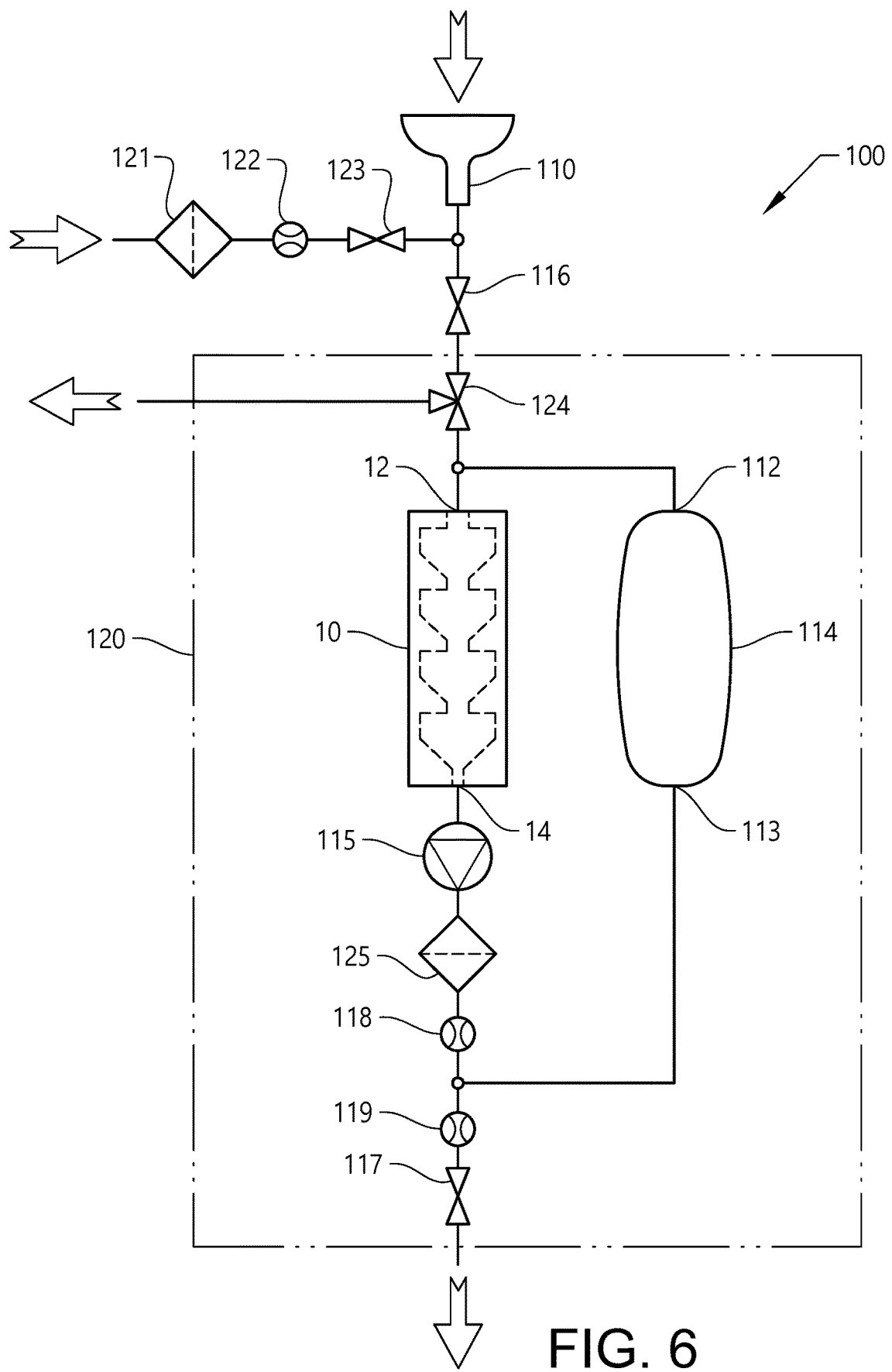
FIG. 6 shows the system 100 of FIG. 3 further comprising a particle filter 121 and a flow meter 122.

FIG. 6 shows the system 100 of FIG. 3 further comprising a particle filter 121 and a flow meter 122.

Figure 7:
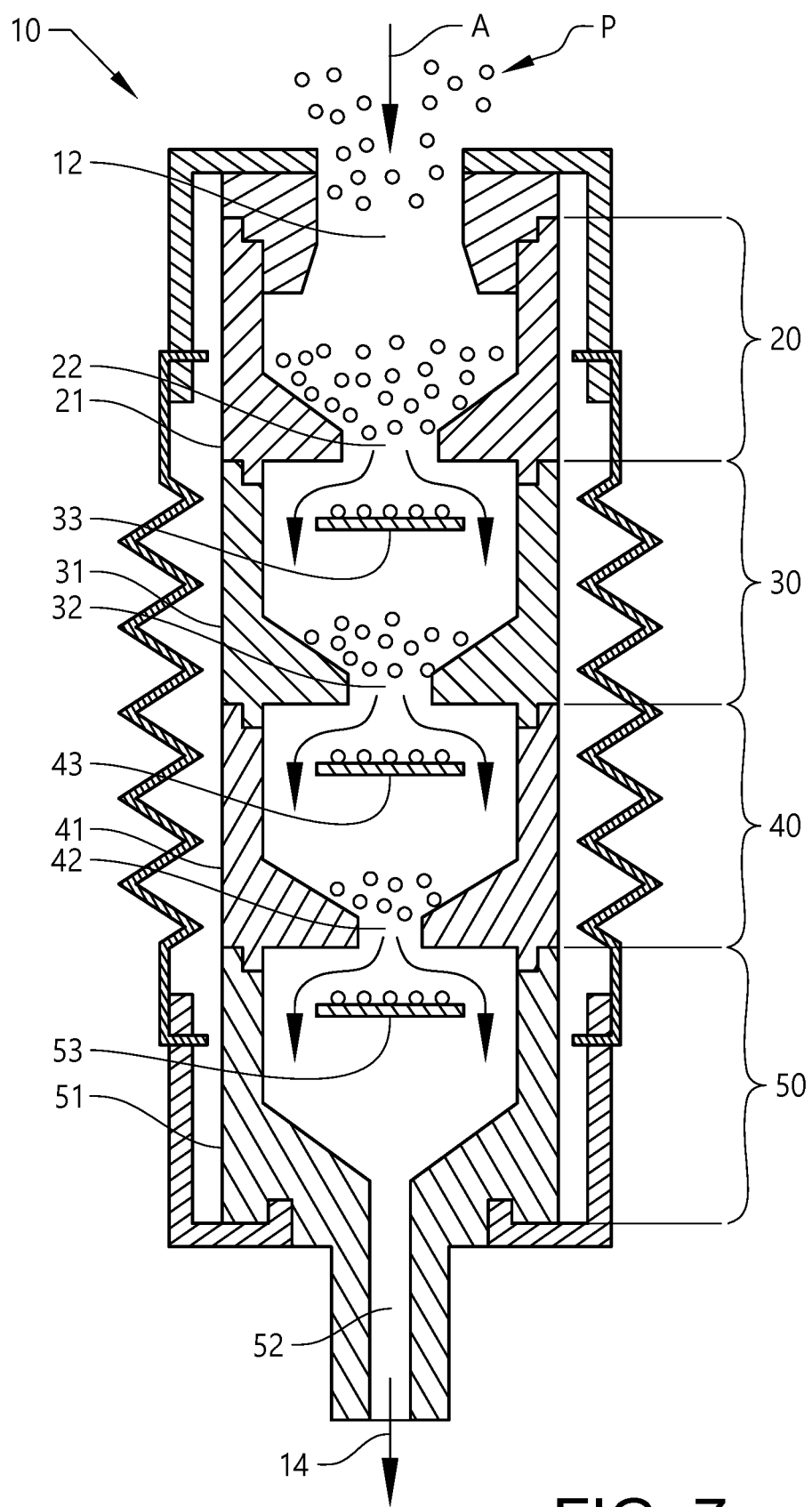
FIG. 7 shows an inertial impactor 10 for collection of exhaled particles.

FIG. 7 shows the inertial impactor 10 comprising a plurality of stages 20, 30, 40, 50. The primary gas stream A comprises air and particles P exhaled by a subject. The flow is caused by a pump 115 connected to the outlet 14 of the impactor. Each stage 20, 30, 40, 50 is separated from adjacent stages by a partition 21, 31, 41, 51. Each partition has at least one orifice 22, 32, 42, 52 (in practise, a plurality of orifices is present in each partition) which directs the gas stream A towards collection plates 33, 43, 53. The major face of each collection plate 33, 43, 53 is arranged substantially perpendicular to the direction of flow of the gas stream A. The collection plates may be as described in this document.

Figure 8:
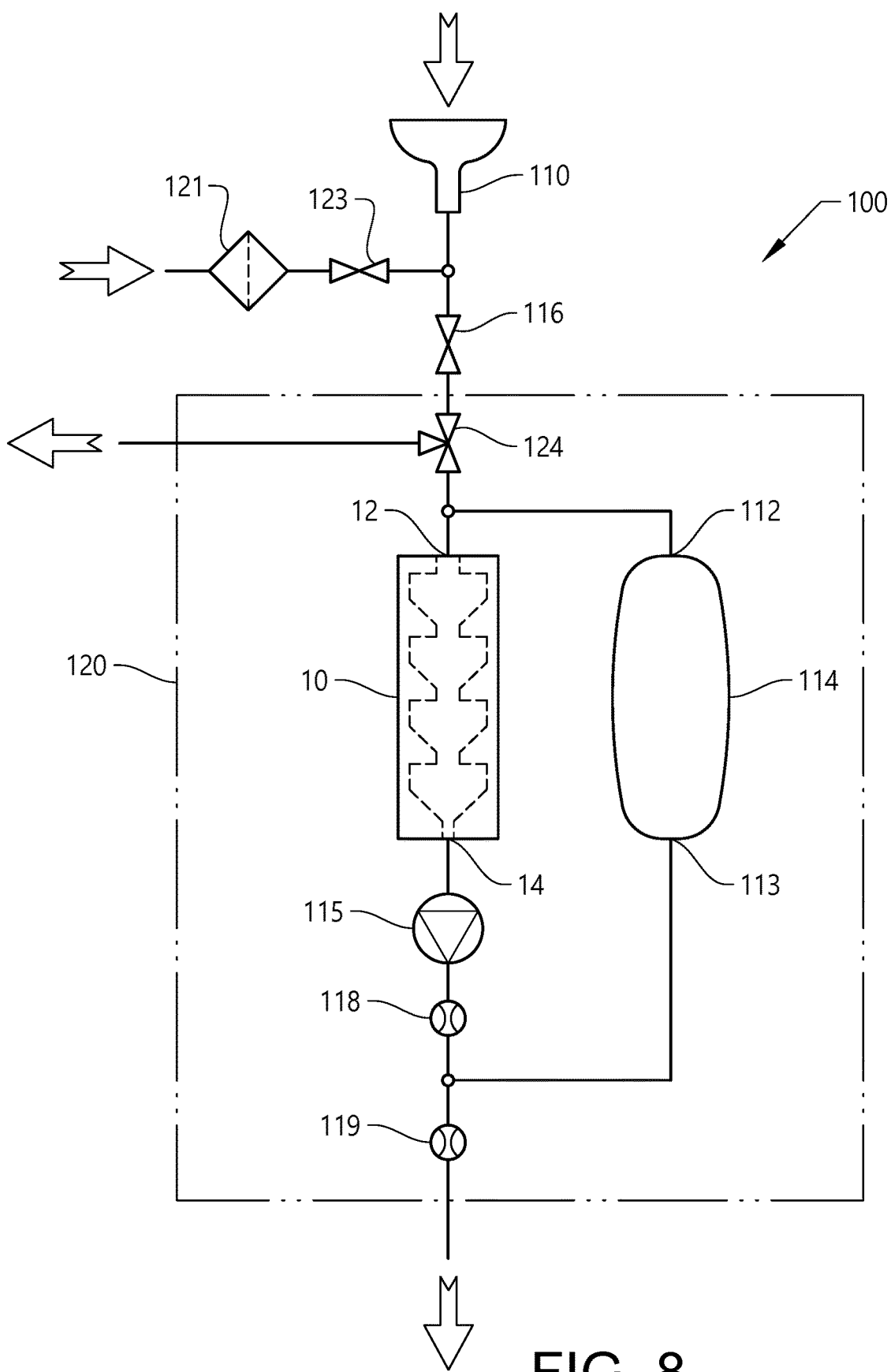
FIG. 8 shows the system of FIG. 4 lacking the flow meter 122 and provided with the valve 124.

FIG. 8 shows the system of FIG. 4 lacking the flow meter 122 and provided with the valve 124.

Figure 9:
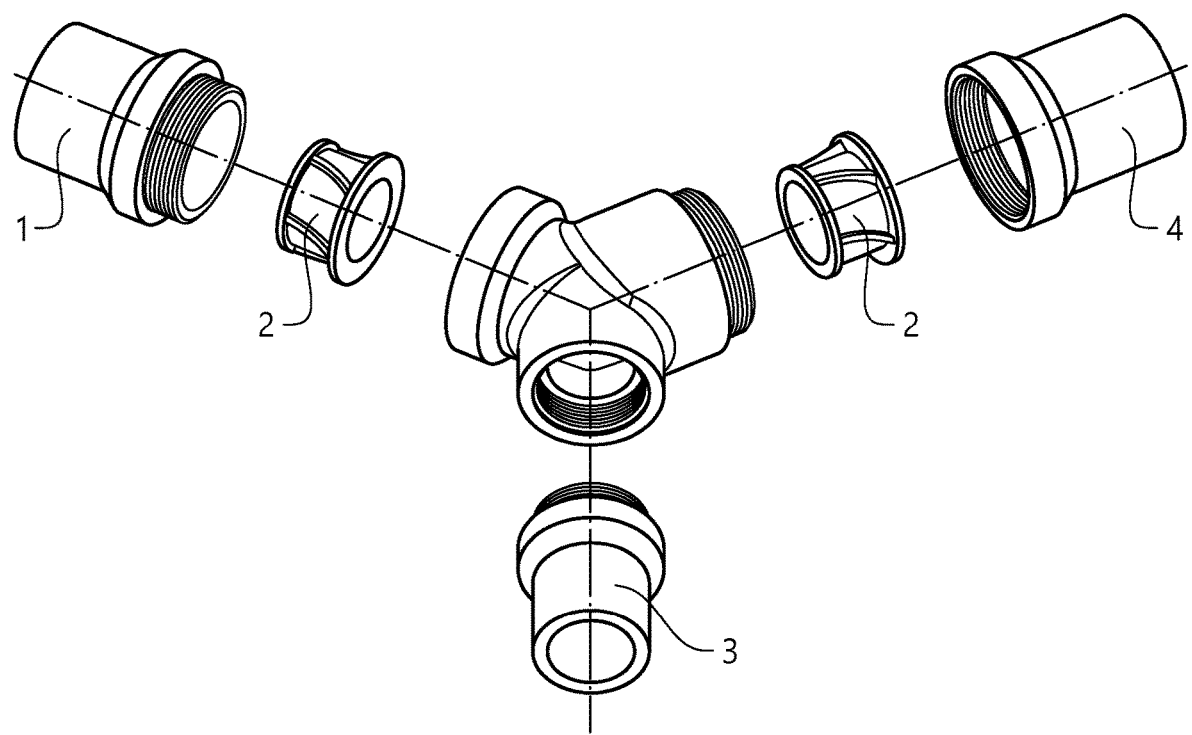
FIG. 9 shows parts that may be put together to provide a three-way coupling element.

FIG. 9 shows parts that may be put together to provide a three-way coupling element. It will be appreciated that may be used instead of the mouthpiece 110 and the line for gas as described herein.

The system 100 may be operated as described below.

The system 100 is arranged to maintain a constant flow of air exhaled through the impactor 10 by means of a pump 115. The air exhaled by the subject passes through the mouthpiece 110 and enters the inertial impactor 10, and also the reservoir 114 since the impactor capacity usually is insufficient for handling an entire exhalation at a time. Thus, the exhaled air exceeding the impactor capacity enters the reservoir 114. Thereafter, the second valve 117, if present, is closed. When the subject finishes his/her exhalation the first valve 116 is closed. The pump 115 will then draw the exhaled air stored in the reservoir 114 through the impactor 10. In this way, a continuous flow of exhaled air through the impactor 10 is maintained and a large part of the exhaled air stored in the reservoir 114 such as most of the stored exhaled air will be drawn through the impactor 10. When a subject then exhales into the system 100 through the mouthpiece 110 the process starts all over again. Thus, it can be seen that a large part such as most or substantially all of the exhaled air is used in the system 100. The full or substantially the full volume of each exhalation of a subject is examined. The system is operated without requiring external air to be added to the reservoir 114 to maintain a flow through the system thereby reducing a risk for contamination associated with added external air.

The mouthpiece 110 is configured to allow a subject exhale air into the system. Prior to exhaling air, the subject may inhale air that has passed through the particle filter 121, the optional flow meter 122, the valve 123 and the mouthpiece 110. The thus inhaled air may subsequently be exhaled through the mouthpiece 110 and the valve 116, and then enter into the impactor 10 and the reservoir 114 being located in the thermostatted part of the system 120. It will be appreciated that the mouthpiece 110, the flow meter 122 and/or the valve 123 may also be thermostatted. For instance, the mouthpiece 110, the flow meter 122 and/or the valve 123 may be located entirely or partly within the thermostatted part of the system 120.

The invention claimed is:

1. A system for collecting exhaled particles, said system comprising:
   a) a reservoir having a first opening and a second opening;
   b) a two-way mouthpiece and a one-way valve configured to open to permit the user to inhale through said mouthpiece via said one-way valve and to close thereafter, thereby preventing outside air from entering the system when the user exhales through said mouthpiece;
   c) an inertial impactor having an inlet and an outlet, said impactor being arranged to pass a gas stream comprising particles between said inlet and said outlet, said inlet of said inertial impactor being connected to said first opening of said reservoir, and said outlet of said inertial impactor being connected to said second opening of said reservoir;
   d) a pump having an inlet and an outlet, said pump being arranged to maintain a constant gas stream flow through said impactor;
   e) a first valve disposed between said mouthpiece and said inertial impactor; and
   f) a further valve disposed between said first valve and said inertial impactor and configured to allow exhaled air to enter said impactor and/or said reservoir, or to be let out of the system, wherein said first opening of said reservoir is connected to said mouthpiece via said first valve and said further valve,
   said pump is located downstream of said impactor,
   said second opening of said reservoir is connected to said outlet of said pump, and
   the system is configured to collect exhaled particles in the exhaled air without permitting outside air to be added to the reservoir.

2. The system according to claim 1 further comprising a second valve, wherein
   said second opening of said reservoir is connected to said outlet of said pump upstream of said second valve.

3. The system according to claim 1, further comprising a first flow meter arranged to measure said gas stream flow through said impactor and said pump.

4. The system according to claim 3, wherein said first flow meter is arranged downstream of said pump.

5. The system according to claim 3, further comprising a second flow meter arranged to measure a total volume of an exhalation by a subject.

6. The system according to claim 1, further comprising a particle counter.

7. The system according to claim 1, wherein said mouthpiece, said impactor and/or said reservoir are thermostatted.

8. The system according to claim 1, wherein said further valve is arranged to be operated manually or is a one-way valve.

9. The system according to claim 1, further comprising a line for gas including a particle filter and another one-way valve.

10. The system according to claim 9, wherein the line for gas further includes a flow meter.

11. A method for detecting a biomarker associated with a medical condition in a patient, comprising the steps of
    collecting exhaled particles from the patient using the system of claim 1; and
    assaying the particles to detect the presence of the biomarker.

12. The method according to claim 11, wherein said biomarker is selected from the group consisting of proteins, phospholipids, bacteria, RNA, and DNA.

13. The method according to claim 11, wherein said medical condition is selected from the group consisting of asthma bronchiale, cystic fibrosis, chronic obstructive pulmonary disease (COPD), interstitial lung-disease, sarcoidosis, pulmonary engagement in systemic disease, pulmonary infections, bacterial colonization, viral infections, heart failure, hypercholesterolemia, diabetes, metabolic syndrome, a condition associated with organ transplant rejection, and increased genetic susceptibility to disease or exposure.

14. The method according to claim 13, wherein the pulmonary infection is pneumonia.

* * * * *